United States Patent
Klaka et al.

(10) Patent No.: US 10,865,380 B2
(45) Date of Patent: Dec. 15, 2020

(54) METHOD FOR IMPROVING THE CULTURE CONDITIONS OF CULTURES OF PRIMARY SWEAT GLAND CELLS AND/OR THREE-DIMENSIONAL SWEAT GLAND EQUIVALENTS

(71) Applicant: Henkel AG & Co. KGaA, Duesseldorf (DE)

(72) Inventors: Patricia Klaka, Leverkusen (DE); Bernhard Banowski, Duesseldorf (DE); Sabine Gruedl, Erkelenz (DE); Thomas Welss, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 429 days.

(21) Appl. No.: 15/834,069

(22) Filed: Dec. 7, 2017

(65) Prior Publication Data
US 2018/0163175 A1 Jun. 14, 2018

(30) Foreign Application Priority Data
Dec. 12, 2016 (DE) .................. 10 2016 224 702

(51) Int. Cl.
C12N 5/071 (2010.01)

(52) U.S. Cl.
CPC ........ *C12N 5/0633* (2013.01); *C12N 2501/11* (2013.01); *C12N 2501/80* (2013.01); *C12N 2513/00* (2013.01)

(58) Field of Classification Search
None
See application file for complete search history.

(56) References Cited

FOREIGN PATENT DOCUMENTS

| CN | 102161981 A | 8/2011 |
|---|---|---|
| DE | 102015222279.9 A1 | 5/2017 |
| DE | 102016217182 A1 | 3/2018 |
| WO | 2014039427 A1 | 3/2014 |

OTHER PUBLICATIONS

Hubka, K. et al., Appl. in vitro Tox., Aug. 2015; vol. 1pp. 187-197.*
Tao, R. et al.: "Isolation, culture, and verification of human sweat gland epithelial cells", Cytotechnology 2010, vol. 62, pp. 489-495; Sep. 18, 2010.
Gao, Y. et al.: "Isolation, culture and phenotypic characterization of human sweat gland epithelial cells", Int. J. Mal. Med. 2014; vol. 34 No. 4, pp. 997-1003; Jun. 26, 2014.
Intellectual Property Office, Search Report under Section 17(5) for United Kingdom Patent Application No. GB1720452.0 dated Sep. 10, 2018.
Bellas et al.: "In Vitro 3D Full-Thickness Skin-Equivalent Tissue Model Using Silk and Collagen Biomaterials"; Macromolecular Bioscience, 2012, 12, Seiten 1627-1636.
Robles, V. et al.: J. Inv. Dermatol, vol. 133, 2013, "Tissue engineering a 3-D functional model of the human eccrine sweat gland", p. S77.
Bovell, D. L. et al.: Eur. J. Pharmacol., vol. 403, 2000, "Nucleotideevoked ion transport and [Ca2+]i changes in normal and hyperhidrotic human sweat gland cells", pp. 45-48.
Wilson, D. C. S. et al.: Veterinary Dermatol., vol. 18, 2007, "A preliminary study of the short circuit current (lsc) responses of sweat gland cells from normal and anhidrotic horses to purinergic and adrenergic agonists", pp. 152-160.

* cited by examiner

*Primary Examiner* — Michael D Burkhart
(74) *Attorney, Agent, or Firm* — Lorenz & Kopf, LLP

(57) ABSTRACT

The present disclosure relates to a method for improving the culture conditions of cultures of primary sweat gland cells and/or three-dimensional sweat gland equivalents, where the culture with from about 500 to about 500,000 sweat gland cells and a diameter of from about 100 to about 6,000 nm is initially prepared and then cultivated in a culture medium with neurotransmitters and/or from about 11 to about 100 ng/ml of at least one growth factor. Cultivation of these cells and models in a culture medium containing at least one neurotransmitter and/or from about 11 to about 100 ng/ml of at least one growth factor leads to an increase of sweat-gland-specific marker proteins. As a result, a loss of function, which occurs with an absence of or only low expression of these markers, can be avoided.

20 Claims, No Drawings

METHOD FOR IMPROVING THE CULTURE CONDITIONS OF CULTURES OF PRIMARY SWEAT GLAND CELLS AND/OR THREE-DIMENSIONAL SWEAT GLAND EQUIVALENTS

CROSS-REFERENCE TO RELATED APPLICATION

This application claims priority to German Patent Application No. 10 2016 224 702.6, filed Dec. 12, 2016, which is incorporated herein by reference in its entirety.

TECHNICAL FIELD

The present disclosure pertains to a method for improving the culture conditions of cultures of primary sweat gland cells and/or three-dimensional sweat gland equivalents, where a culture of primary sweat gland cells and/or three-dimensional sweat gland equivalents with from about 500 to about 500,000 sweat gland cells and a diameter of from about 100 to about 6,000 μm is initially prepared and then cultivated in a culture medium containing at least one neurotransmitter and/or at least 11 ng/ml of growth factor. Cultivation of these cells and models in a culture medium containing at least one neurotransmitter and/or at least 11 ng/ml of growth factor achieves an increase of sweat-gland-specific marker proteins in comparison to cultivation without the addition of neurotransmitter(s) and/or at least 11 ng/ml of growth factor(s). As a result, a loss of function of the cultivated cells, which occurs with an absence of or only low expression of these markers, can be avoided.

Furthermore, the present disclosure relates to the use of at least one neurotransmitter and/or at least one growth factor for improving the culture conditions of cultures of primary sweat gland cells and/or three-dimensional sweat gland equivalents. The addition of these compounds achieves an increase of sweat-gland-specific marker proteins and a loss of function of the cultivated cells is avoided in this manner.

Washing, cleaning and care for the body are a basic human need and modern industry continuously attempts to meet these human needs in a variety of ways. Long-lasting elimination or at least reduction of the body odor and underarm wetness are especially important for daily hygiene. Underarm wetness and body odor occur due to secretion of eccrine and apocrine sweat glands in the human armpits. While the eccrine glands serve for thermal regulation of the body and are responsible for the production of underarm wetness, the apocrine glands release a viscous secretion in reaction to stress, from which unpleasant odor is produced due to bacterial decomposition.

Initial research work on native eccrine and apocrine sweat glands was already conducted at the beginning of the 20th century in order to classify these skin appendages belonging to this group of exocrine glands. Sweat glands can be classified as apocrine and eccrine sweat glands, as well as a mixed form of apocrine and eccrine sweat glands (also referred to as an apoeccrine sweat gland). The forms mentioned above can differ based on morphologic and characteristic features.

The eccrine sweat gland, particularly the human eccrine sweat gland, belongs to the unbranched wound tubular glands and can be classed as the secretory end piece (also referred to as coil), the dermal execution path (also referred to as duct) and the epidermal execution path (also referred to as acrosyringium). The cells present in these glandular sections have different tasks and functions, such as secretion in the coil, re-absorption of ions in the duct and delivery of the secretion, particularly of the sweat, to the surrounding skin by the acrosyringium. The eccrine sweat glands are mainly stimulated by the neurotransmitter acetylcholine (ACh), but a purinergic (for example by ATP/UTP) and an αβ-adrenergic (for example by noradrenaline) stimulation are also possible.

With regard to the prevention of underarm wetness and/or body odor, it is therefore desirable to reduce and/or avoid the secretion from eccrine and/or apocrine sweat glands. This can be achieved, for example, by virtue of the fact that the execution paths of the eccrine sweat glands become blocked by employing so-called plugs. For this purpose, antiperspirant aluminum and/or aluminum-zirconium salts are used in the prior art, which, however, are perceived as critical by the consumer. Furthermore, antibacterial agents which inhibit the bacterial decomposition of sweat are used in the prior art. However, such agents can negatively influence the natural microflora of the skin under the armpits. It is therefore desirable to provide cosmetic agents which are capable of reliably preventing underarm wetness and/or body odor and which are free of aluminum and/or aluminum-zirconium salts and compounds having anti-bacterially active compounds. A possibility for providing such agents is the use of substances which effectively inhibit the stimulation and/or biological processes of sweat glands and thus prevent and/or avoid sweat secretion. In vivo tests can be conducted with test participants in order to identify such substances. However, such tests are elaborate and do not permit screening processes with high throughput rates. Furthermore, in vitro tests using cell cultures and/or cell models of sweat glands can be used, wherein the influence of test substances on the stimulation of the sweat glands can be investigated.

So that the test results obtained in vitro can be transferred well to the in vivo situation, the cells or cell models of the sweat gland which are used must simulate the in vivo situation as accurately as possible. For this purpose, it is desirable that the largest possible amount of sweat-gland-specific marker proteins is expressed in the cell cultures and/or cell models. However, the conditions for cultivation of sweat gland cells and their cell modules known thus far result in an only minor expression of the marker proteins mentioned above.

Therefore, there is a need for a method for optimizing the culture conditions of cell cultures and/or cell models of sweat gland cells in order to increase the expression of marker proteins specific to sweat glands.

Therefore, the present disclosure is based on the task of providing a method for optimizing the culture conditions of cell cultures and/or cell models of sweat gland cells.

BRIEF SUMMARY

Methods for improving culture conditions and for growing cultures are provided. In an exemplary embodiment, a method for improving culture conditions of primary sweat glands and/or three-dimensional sweat gland equivalents includes preparing at least one culture of the primary sweat glands and/or three-dimensional sweat gland equivalents with from about 500 to about 500,000 sweat gland cells and a diameter of from about 100 to about 6,000 micrometers. The cell culture is cultivated in a culture medium that includes at least one neurotransmitter and/or from about 11 to about 100 nanograms per milliliter of a least one growth factor.

In another embodiment, a method for growing cultures of primary sweat glands and/or three-dimensional sweat gland equivalents is provided. The method includes using at least one neurotransmitter and/or at least one growth factor for improvement of culture conditions of the cultures. The cultures of primary sweat glands and/or three-dimensional sweat gland equivalents has from about 500 to about 500,000 sweat gland cells and a diameter of from about 100 to about 6,000 micrometers.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now been found to be surprising that the addition of at least one neurotransmitter and/or at least 11 ng/ml of growth factor to the culture medium during the cultivation of the cell cultures and/or cell models of sweat gland cells leads to an increase in the expression of sweat-gland-specific marker proteins. In this way, a loss of function of these marker proteins in the culture can be avoided and the in vivo situation can be reproduced in an improved manner.

Therefore a first subject of the present disclosure is a method for improving the culture conditions of cultures of primary sweat gland cells and/or three-dimensional sweat gland equivalents, comprising the following method steps.
a) Preparation of at least one culture of primary sweat gland cells and/or at least one three-dimensional sweat gland equivalent with from about 500 to about 500,000 sweat gland cells and a diameter of from about 100 to about 6000 µm,
b) Cultivation of the at least once cell culture of primary sweat gland cells and/or at least one three-dimensional sweat gland equivalent in a culture medium prepared under step a), which
b1) contains at least one neurotransmitter and/or
b2) from about 11 ng/ml to about 100 ng/ml of at least one growth factor.

The addition of at least one neurotransmitter and/or from about 11 to about 100 ng/ml of at least one growth factor during cultivation of the sweat gland cells and/or sweat gland equivalent leads to an increased expression of sweat-gland-specific marker proteins, such as aquaporin-5. Aquaporin-5 (AQPS) is a water channel protein which plays a role in the formation of sweat. Due to the increased expression of such proteins, a loss of function within the cell cultures is avoided and, in this way, the in vivo situation is better reproduced. Therefore, the results achieved with these cultures in relation to the effectiveness of antiperspirant compounds translate better to the in vivo situation.

As contemplated herein, the term "improvement of the culture conditions" is understood to mean the increase in the expression of marker proteins specific to sweat glands, such as aquaporin 5, by using neurotransmitters and/or from about 11 to about 100 ng/ml of at least one growth factor. For this purpose, cultures which have been treated with the aforementioned compounds during the cultivation are preferably treated with cultures which were cultivated without addition of these compounds.

Furthermore, as contemplated herein, a three-dimensional sweat gland equivalent is understood to mean a cell model of glandular cells which has an extent in all three spatial directions and in which the cells have a similar function, particularly an identical function as the cells of a native sweat gland.

Furthermore, a culture medium that is also referred to as a nutrient medium is used, preferably a liquid medium for cultivating the primary sweat gland cells and/or three-dimensional sweat gland equivalents.

As contemplated herein, a neurotransmitter is understood to mean a compound which is capable of stimulating or inhibiting a neuroreceptor (also referred to as a membrane receptor protein). A specific binding to the corresponding membrane proteins takes place based on the structure and charge distribution of the neurotransmitter. The binding of the neurotransmitter triggers a conversion of the receptor protein. This transformation either directly (also referred to as ionotropic) or indirectly (also referred to as metabotropic) results in the opening of specific ion channels of the cell in this region. The strength of the ion currents is dependent on the number of bound neurotransmitters. As a rule, the binding of the neurotransmitter to the membrane receptor molecules is reversible, so that only a temporary opening of the ion channels takes place.

Ultimately, growth factors as contemplated herein, are understood to mean proteins which are used for signal transmission between cells. In this case, the signal is transmitted by binding the growth factor to a specific receptor on the surface of the cell membrane. The growth factors can either be released from the cell into the environment or be membrane-bound. When the growth factor is bound to the corresponding receptor, a conformational change of this receptor takes place. This conformational change triggers signals in the interior of the cell which, for example, lead to activation or disconnection of genes via further signal transmissions.

In method step a) of the method as contemplated herein, a culture of primary sweat gland cells and/or a three-dimensional sweat gland equivalent is prepared. This three-dimensional sweat gland equivalent has a specific number of cells and a specific diameter.

As contemplated herein, it is advantageous if the culture of primary sweat gland cells is specific cultures. Preferred embodiments of the present disclosure are wherein the at least one culture prepared in method step a) is a monolayer culture of said sweat gland cells. Use of such monolayer cultures leads to an especially high expression of sweat-gland-specific marker proteins with addition of neurotransmitters and/or about 11-100 ng/ml of growth factors.

In order to guarantee good comparability with the in vivo situation, monolayer cultures which are produced from eccrine and/or apocrine human sweat glands are preferably used in method step a). As contemplated herein, therefore, it is advantageous if the at least one culture of primary sweat gland cells prepared in method step a) is an eccrine and/or apocrine human primary monolayer culture of said sweat gland cells. Cultures of this type can be obtained, for example, by isolating native eccrine and/or apocrine sweat glands from human skin biopsies by employing enzymatic digestion and production of a cell preparation from these isolated sweat glands. This cell preparation is used for production of the monolayer cultures used in method step a).

In method step a) of the method, at least one three-dimensional sweat gland equivalent can also be prepared instead of or in addition to the culture of primary sweat glandular cells. These sweat gland equivalents have a diameter of from about 100 to about 6,000 µm. However, it has been found to be advantageous within the scope of the present disclosure, if the prepared three-dimensional sweat gland equivalents have smaller diameters. Therefore, as contemplated herein it is advantageous if the at least one three-dimensional sweat gland equivalent prepared in method step a) has a diameter of from about 100 to about 4000 μm, preferably from about 100 to about 2000 μm, particularly from about 200 to about 1500 μm. The diameter of the preferred spherical sweat gland equivalents can, for example, be determined by employing microscopic measurement using the software "CellSens", wherein the above values relate to the diameter on the widest and/or longest point of an individual sweat gland equivalent.

In the context of the present disclosure, it is preferable if the sweat gland equivalents prepared in method step a) are free from matrix compounds and/or carriers. In this context, such matrix compounds are to be understood as meaning compounds which are capable of forming spatial networks. However, this does not include the substances produced and separated from the cells of the equivalents themselves, which are capable of forming spatial networks. Furthermore, carriers in the sense of the present disclosure are self-supporting substances which can serve as a foundation or framework for the sweat gland cells. According to a preferred embodiment of the present disclosure, the at least one three-dimensional sweat gland equivalent prepared in method step a) is free from matrix compounds and/or carriers, particularly free from matrix compounds and carriers.

The term "free from" in the context of the present disclosure is understood to mean that the three-dimensional sweat gland equivalent contains less than about 1 wt. % of matrix compounds and/or carriers relative to the total weight of the three-dimensional sweat gland equivalent. Therefore, in the scope of the present disclosure, it is advantageous if the three-dimensional sweat gland equivalents prepared in method step a) contain from about 0 to about 1 wt. %, preferably from about 0 to about 0.5 wt. %, more preferably from about 0 to about 0.2 wt %, particularly about 0 wt. % of matrix compounds and carriers relative to the total weight of the three-dimensional sweat gland equivalent in each case.

In this context, it is especially advantages if the three-dimensional sweat gland equivalents prepared in method step a) are free from specific matrix compounds and carriers. Therefore, it is preferred if the three-dimensional sweat gland equivalent does not contain any matrix compounds and/or carriers which are selected from the group of collagens, particularly collagens of type I and/or type III and/or type IV, scleroproteins, gelatins, chitosans, glucosamines, glucosaminoglucanes (GAG), heparinsula proteoglycans, sulfated glycoproteins, growth factors, crosslinked polysaccharides, crosslinked polypeptides, and mixtures thereof. It is particularly preferable that the three-dimensional sweat gland equivalent prepared in method step a) is an equivalent of the eccrine and/or apocrine human sweat gland. Preferred embodiments of the present disclosure are therefore wherein the at least one three-dimensional sweat gland equivalent prepared in method step a) is a three-dimensional sweat gland equivalent of the eccrine and/or apocrine human sweat gland. The in vivo situation in the human sweat gland can be reproduced particularly well with sweat gland equivalents of this type.

Furthermore, as contemplated herein it is especially preferred if the three-dimensional sweat gland equivalent prepared in method step a) was produced from human eccrine and/or apocrine sweat glands. Therefore, it is advantageous in the context of the present disclosure if the at least one three-dimensional sweat gland equivalent prepared in method step a) is a three-dimensional sweat gland equivalent obtained from eccrine and/or apocrine native human sweat gland cells.

Furthermore, as contemplated herein it has been found to be advantageous if the three-dimensional sweat gland equivalents prepared in method step a) have at least one specific cell type. Use of such equivalents lead to an especially good simulation of the in vivo situation. Therefore, preferred embodiments of the present disclosure are wherein the at least one three-dimensional sweat gland equivalent prepared in method step a) contains at least one cell type selected from the group of (i) coil cells, particularly clear cells, dark cells and myoepithelium cells, (ii) duct cells and (iii) mixtures thereof. As contemplated herein, the term "clear cells" is understood to mean cells which have a clear and/or uncolored cytoplasm when stained with dyes, particularly with hematoxylin and eosin. "Clear" cells of this type are preferably secretory cells of the epithelium which are preferably in contact with the lumen. The plasma membrane of these cells is folded strongly on the apical and lateral surface. The cytoplasm of these "clear cells" contains high quantities of glycogen and mitochondria. The aqueous component of sweat which contains electrolytes and inorganic substances is preferably separated from this cell type. By contrast, the "dark cells" mentioned above are cells, the vacuoles of which have a positive staining on mucopolysaccharide acid, the cytoplasm of which can thus be stained by dyes. These "dark cells" are in contact with the basal membrane and have only few mitochondria in comparison to the "clear cells". Macromolecules, such as glycoproteins, are preferably separated from these "dark cells". The term "myoepithelial cells" mentioned above is to be understood as contractile epithelial cells, which have a cytoskeleton with so-called gap junctions and can therefore contract. The secretion from the gland end pieces is supported in this manner. Such cells are preferably found between the basal membrane and the "clear cells" and "dark cells" mentioned above. Finally, as contemplated herein, the term "duct cells" is understood to mean cells which form the wall of the duct and have a stratified cubic epithelium. The cell types mentioned above can, in addition to staining using hematoxylin and eosin, also be determined by employing immunocytochemical staining using markers specific for these cells. A specific marker that can be used for myoepithelial cells is, for example, the alpha-smooth muscle actin (also referred to as α-SMA). Substance P and S100, for example, are suitable as specific markers for "clear cells". Furthermore, the specific marker cytokeratin 10 (also referred to as CK10) and CD200 can be used for "dark cells" of the markers known by the name CGRP (calcitonin-gene related peptide) and for duct cells.

Particularly preferred three-dimensional sweat gland equivalents prepared in method step a) are described below. Therefore, a particularly preferred embodiment of this method step is the preparation of a three-dimensional sweat gland equivalent of the eccrine and/or apocrine human sweat glands comprising from about 500 to about 500,000 sweat gland cells, wherein the three-dimensional sweat gland equivalent has a diameter of from about 200 to about 1500 μm.

Furthermore, a particularly preferred embodiment of this method step is the preparation of a three-dimensional sweat gland equivalent obtained from eccrine and/or apocrine native human sweat gland cells comprising from about 500 to about 500,000 sweat gland cells, wherein the three-dimensional sweat gland equivalent has a diameter of from about 200 to about 1500 μm.

Moreover, a particularly preferred embodiment of this method step is the preparation of a three-dimensional sweat gland equivalent comprising from about 500 to about 500, 000 sweat gland cells, wherein the three-dimensional sweat gland equivalent has a diameter of from about 200 to about 1500 µm and at least one cell type selected from the group of clear cells, dark cells, myoepithelium cells, duct cells and mixtures thereof.

Furthermore, a particularly preferred embodiment of this method step is the preparation of a three-dimensional sweat gland equivalent obtained from eccrine and/or apocrine native human sweat gland cells comprising from about 500 to about 500,000 sweat gland cells, wherein the three-dimensional sweat gland equivalent has a diameter of from about 200 to about 1500 µm and at least one cell type selected from the group of clear cells, dark cells, myoepithelium cells, duct cells and mixtures thereof.

Moreover, a particularly preferred embodiment of this method step is the preparation of a three-dimensional sweat cell equivalent of the eccrine and/or apocrine human sweat gland comprising from about 500 to about 500,000 sweat gland cells, wherein the three-dimensional sweat gland equivalent has a diameter of from about 200 to about 1500 µm and contains about 0 wt. % of matrix compounds and carriers relative to the total weight of the three-dimensional sweat gland equivalent.

Furthermore, a particularly preferred embodiment of this method step is the preparation of a three-dimensional sweat gland equivalent of the eccrine and/or apocrine human sweat gland comprising from about 500 to about 500,000 sweat gland cells, wherein the three-dimensional sweat gland equivalent has a diameter of from about 200 to about 1500 µm and contains about 0 wt. % of matrix compounds and carriers relative to the total weight of the three-dimensional sweat gland equivalent, wherein the matrix compounds and/or carriers are selected from the group of collagens, particularly collagens of type I and/or type III and/or type IV, scleroproteins, gelatins, chitosans, glucosamines, glucosaminoglucanes (GAG), heparinsulfate proteoglucans, sulfated glycoproteins, growth factors, cross-linked polysaccharides, cross-linked polypeptides and mixtures thereof.

The monolayer cultures of sweat gland cells and the three-dimensional sweat gland equivalents prepared in method step a) can be produced, for example, in the method steps described below.

In a first step, isolated sweat glands which can be obtained from skin biopsies or similar processes and which were removed from their natural environment are prepared. These sweat glands are preferably obtained by isolating native sweat glands, particularly native eccrine and/or apocrine sweat glands, from human skin, wherein the isolation of the native sweat glands preferably takes place by enzymatic digestion of the human skin using a mixture of from about 2 to about 3 mg/ml collagenase II and from about 0.1 to about 0.2 mg/ml of thermolysin for from about 3 to about 6 hours at from about 35 to about 40° C., particularly 37° C.

A cell culture is produced from these isolated sweat glands by cultivation. A particularly good cultivation of the isolated sweat glands is achieved if a mixture of DMEM and Ham's F12 in the weight ratio of 3:1, which contains an additional about 10 wt. % of fetal calf serum (FCS) relative to the total weight of the mixture, is used as a nutrient medium. The cultivation of these sweat glands in the nutrient medium described above preferably takes place for from about 7 to about 28 days, particularly for 14 days, at a temperature of from about 36 to about 38° C. and a $CO_2$ content of about 5 wt. % relative to the total weight of the atmosphere used for cultivation.

In order to obtain the cultures of primary sweat gland cells prepared in method step a), the sweat gland cells which have grown out the isolated sweat glands are detached and re-cultivated.

To produce the three-dimensional sweat gland equivalents, a cell preparation is used which is obtained by detaching the sweat gland cells that grew out of the isolated sweat glands, cultivation of these cells in monolayer cultures and separation and suspension in nutrient medium. The cell preparation preferably contains a cell count of primary sweat gland cells of from about 50 to about 2500 cells per µL nutrient medium, particularly from about 400 to about 600 cells per µL of nutrient medium. In order to obtain the three-dimensional sweat gland equivalent, from about 10 to about 100 µL, particularly from about 40 to about 60µ, of this cell preparation is cultivated in a suspended state, in other words, in the form of a droplet hanging freely from a surface. In this connection, the use of so-called hanging-drop-wells such as commercially available, for example, from the company Insphero as GravityPLUS® sowing plate with SureDrop® introduction system and GravityTRAP® harvesting plate. In the process, it is preferred if 40 volume percent of the nutrient medium of the cell preparation relative to the total volume of the aforementioned cell preparation is replaced with fresh nutrient medium during the cultivation period, particularly after from about 1 to about 3 days. The obtained equivalents are isolated by adding from about 50 to about 200 µL of nutrient medium and can be cultivated according to method step b). However, it can also be stipulated that the isolated equivalents are re-cultivated before method step b) is carried out.

The three-dimensional sweat gland equivalents prepared in method step a) are preferably produced using in vitro methods exclusively. Therefore, these equivalents can also be used to test substances which are intended for cosmetic use. Furthermore, this production process enables affordable production of standardized equivalents which can be used in screening processes with high throughput rates. This production method also results in three-dimensional sweat gland equivalents forming ordered structures and having differently differentiated cells. The result is a good reproduction of the in vivo situation.

A production process for the three-dimensional sweat gland equivalents prepared in method step a) of the method is disclosed, for example in the German patent application DE 10 2015 222 279, the content of which is fully incorporated by reference.

In the second method step b) of the method, cultivation of the cell culture of primary sweat gland cells and/or the three dimensional sweat gland equivalents prepared in method step a) takes place, wherein the culture medium used for this cultivation contains at least one neurotransmitter and/or from about 11 to about 100 ng/ml of at least one growth factor. In this context, the quantity of from about 11 to about 100 ng/ml relates to the total concentration of growth factor(s) in the nutrient medium.

In the context of the present disclosure, it has been found to be particularly advantageous if only one neurotransmitter or from about 11 to about 100 ng/ml of at least one growth factor is added to the culture medium used in method step b). Preferred embodiments of the present disclosure are therefore wherein the culture medium used in method step b) contain exactly one neurotransmitter or from about 11 to about 100 ng/ml of exactly one growth factor. The use of a culture medium containing only one neurotransmitter or from about 11 to about 100 ng/ml of exactly one growth factor has been found to be particularly advantages with regard to the expression of sweat-gland-specific marker proteins of the cultivated cells and/or equivalents.

A mixture of DMED (also referred to as Dulbecco's Modified Eagle Medium) and Ham's F12 in a volume ration of 3:1, which also contains about 10 wt. % of fetal calf serum (FCS) is preferably used as a culture medium. This culture medium can also contain additional components selected from the group of hydrocortisone, insulin, choleratoxin, adenine, gentamicin, penicillin G, triiodothyronine and ascorbyl-2-phosphate, as well as mixtures thereof. The addition of these additional components has been found to be advantageous in the context of the present disclosure with regard to the growth of primary sweat gland cells and three-dimensional sweat gland equivalents.

In the context of the present disclosure, it is preferable if the culture medium used in method step b) contains specific neurotransmitters. Therefore, as contemplated herein, it is preferable if the at least one neurotransmitter, particularly the exactly one neurotransmitter is selected from the group of compounds that bond on metabotropic and/or ionotropic receptors, particularly from the group of muscarinic transmitters, αβ-adrenergic transmitters, purinergic transmitters and mixtures thereof. Use of the aforementioned neurotransmitters has been found to be particularly advantageous with regard to the increase of the expression of sweat-gland-specific marker proteins. In this context, metabotropic receptors are understood to mean receptors on the surface of the cell membrane which indirectly lead to the opening of ion channels with the bonding of the neurotransmitter. By contrast, the bonding of these neurotransmitters on ionotropic receptors leads to a direct opening of the ion channels based on the neurotransmitter bond.

In this context, it is particularly advantageous if the muscarinic neurotransmitters is selected from acetylcholine and its analogs. Preferred embodiments of the present disclosure are wherein the muscarinic transmitter is selected from the group of acetylcholine, acetylcholine analogs and mixtures thereof, particularly acetylcholine. As contemplated herein, the term acetylcholine analogs is understood to mean chemical compounds which have a structural or functional similarity to acetylcholine and therefore also trigger an opening of ion channels when bonding on the aforementioned receptors. Examples of the acetylcholine analogs as contemplated herein are pilocarpin and carbachol. As contemplated herein, however, it is preferable if the culture medium used in method step b) has at least one, particularly exactly one, neurotransmitter from the group of muscarinic transmitters, particularly acetylcholine. The use of only acetylcholine in method step b) has been found to be particularly advantageous with regard to the increase of the expression of sweat-gland-specific marker proteins and therefore leads to a particularly high improvement of culture conditions of primary sweat gland cells and three-dimensional sweat gland equivalents.

Furthermore, it can also be stipulated in this context that the culture medium used in method step b) contains a special αβ-adrenergic transmitter. Therefore, it can be preferable as contemplated herein if the αβ-adrenergic transmitter is selected from the group of catecholamines, catecholamine analogs and mixtures thereof, in particular noradrenaline The term catecholamine analogs in the context of the disclosure is understood to mean chemical compounds having a structural or functional similarity to catecholamines. Particularly good results with regard to the improvement of the cultivation conditions are achieved in the context of the disclosure if the culture medium used in method step b) contains at least one, particularly exactly one, neurotransmitter from the group of αβ-adrenergic transmitters, particularly noradrenaline.

Furthermore, in this context it can also be stipulated that the purinergic transmitter is selected from specific nucleosides and phosphorylated nucleotides. Preferred embodiments of the present disclosure are therefore wherein the purinergic transmitter is selected from the group of nucleosides and phosphorylated nucleotides, particularly from adenosine, adenosine diphosphate (ADP), adenosine triphosphate (ATP), urinosine diphosphate (UDP), urinosine triphosphate (UTP) and urinosine diphosphate glucose (UDP glucose). In the context of the present disclosure, nucleotides are understood to mean chemical compounds of a nucleobase and a pentose and, unlike the nucleotides, do not contain any phosphate residues. An example of this is adenosine, which includes the nucleobase adenine and the pentose β-D-ribose. By contrast, nucleotides as contemplated herein are compounds which contain at least one phosphate residue in addition to a nucleobase and a pentose. Examples of this are adenosine phosphate (ADP), adenosine triphosphate (ATP), urinosine diphosphate (UDP), urinosine triphosphate (UTP) and urinosine diphosphate glucose (UDP glucose). In the context of the present disclosure, it has been found to be advantageous with regard to the increase of the expression of sweat-gland-specific marker proteins and thus with regard to the improvement of the cultivation conditions if the nutrient medium contains adenosine triphosphate (ATP) as the only purinergic transmitter.

In the context of the present disclosure it has also been found to be beneficial if the culture medium used in method step b) contains the at least one neurotransmitter in a specific total concentration. As contemplated herein, therefore, it is preferred if the culture medium used in method step b) contains the at least one neurotransmitter in a total concentration of from about 2.0 μM to about 30 mM, preferably from about 2.0 μM to about 28 mM, more preferably from about 2.0 μM to about 25 mM, particularly from about 2.0 μM to about 20 mM. The concentrations indicated above relate to the totality of neurotransmitters used, which means the concentrations indicated above relate to the total concentration of the mixture used when a mixture of different neurotransmitters is used. With use of the total concentrations of neurotransmitter(s) indicated above in the culture medium of method step b), an especially high increase of the gene expression of sweat-gland-specific marker proteins is achieved in comparison to cultures which were cultivated without the addition of neurotransmitter(s). In this manner, the loss of function of the cells, which can occur with a lower expression of these marker proteins, can be avoided.

If a muscarinic transmitter, particularly acetylcholine and/or a purinergic transmitter, particularly adenosine triphosphate (ATP), is used as a neurotransmitter, it has been found to be beneficial in this context if these transmitters are contained in the concentration ranges in the nutrient medium of methods step b) indicated below. As contemplated herein, therefore, it is preferred if the exactly one muscarinic neurotransmitter, particularly acetylcholine is contained in a total concentration of from about 2.0 μM to about 50 μM. Furthermore, it is preferred as contemplated herein if the exactly one purinergic neurotransmitter, particularly adenosine triphosphate (ATP) is contained in a total concentration of from about 0.3 to about 20 mM.

Preferred culture media used in method step b) is therefore described by the following embodiments AF1 to AF10:

AF1: Culture medium containing at least one neurotransmitter, selected from the group of muscarinic transmitters, αβ-adrenergic transmitters, purinergic transmitters and mixtures thereof, AF2: Culture medium containing at least one neurotransmitter, selected from the group of muscarinic transmitters, αβ-adrenergic transmitters, purinergic transmitters and mixtures thereof in a total concentration of from about 2.0 µM to about 30 mM, preferably from about 2.0 µM to about 28 mM, more preferably from about 2.0 µM to about 25 mM, particularly from about 2.0 µM to about 20, AF3: Culture medium containing exactly one neurotransmitter, selected from muscarinic transmitters, AF4: Culture medium containing exactly one neurotransmitter, selected from muscarinic transmitters in a total concentration of from about 2.0 µM to about 50

AF5: Culture medium containing at least one neurotransmitter, selected from muscarinic transmitters in a total concentration of from about 2.0 µM to about 50 wherein the muscarinic transmitter is acetylcholine, AF6: Culture medium contains exactly one neurotransmitter, selected from αβ-adrenergic neurotransmitters, AF7: Culture medium contains exactly one neurotransmitter, selected from αβ-adrenergic neurotransmitters, wherein the αβ-adrenergic transmitter is noradrenaline, AF8: Culture medium containing exactly one neurotransmitter, selected from purinergic transmitters, AF9: Culture medium containing exactly one neurotransmitter, selected from purinergic transmitters in a total concentration of from about 0.3 µM to about 20 mM, AF10: Culture medium containing at least one neurotransmitter, selected from purinergic transmitters in a total concentration of from about 0.3 µM to about 20 mM, wherein the purinergic transmitter is adenosine triphosphate (ATP), In addition to or instead of the at least one neurotransmitter, the culture medium used in method step b) contains from about 11 to about 100 ng/ml of at least one growth factor. It has been found in the context of the present disclosure that use of specific growth factors is preferred. Therefore, advantageous embodiments of the present disclosure are wherein the at least one growth factor, particularly the exactly one growth factor is selected from epidermal growth factor (EGF). The use of EGF, particularly the exclusive use of EGF in a total concentration of from about 11 to about 100 ng/ml in the culture medium of method step b) has been found to be especially advantageous with regard to the increase of the expression of sweat-gland-specific marker proteins and therefore with regard to the improvement of the culture conditions of primary sweat gland cells and three-dimensional sweat gland equivalents.

In the context of the present disclosure it is also preferred if the culture medium used in method step b) contains the at least one growth factor in a lower total concentration. Therefore, it is preferred as contemplated herein if the culture medium used in method step b) contains the at least one growth factor, particularly epidermal growth factor (EGF), in a total concentration of from about 11 ng/ml to about 80 ng/ml, preferably from about 11 ng/ml to about 60 ng/ml, more preferably from about 11 ng/ml to about 40 ng/ml, particularly from about 15 ng/ml to about 25 ng/ml. The concentrations indicated above relate to the totality of growth factors used and/or the use of EGF as a growth factor in this context. With use of the total concentrations of growth factor(s) indicated above in the culture medium of method step b), an especially high increase of the gene expression of sweat-gland-specific marker proteins is achieved in comparison to cultures which were cultivated without the addition of growth factor(s). In this manner, the loss of function of the cells, which can occur with a lower expression of these marker proteins, can be avoided.

The cultivation takes place preferably in method step b) of the method for a specific duration of time. It is been found to be advantageous as contemplated herein if the cultivation in method step b) takes place for a duration of from about 4 h to about 25 days, particularly from about 4 h to about 72 h.

In the context of the present disclosure, it can also be stipulated that a specific percent by volume of the culture medium is replaced with fresh culture medium after a specific time during the cultivation in method step b). In this context, fresh culture medium is understood to mean a medium which does not contain any cells, but at least one neurotransmitter and/or from about 11 to about 100 ng/ml of at least one growth factor. The percent by volume in this context relates to the total volume of the culture medium used in method step b). Therefore, as contemplated herein, it is advantageous if from about 20 to about 60 vol. %, particularly from about 40 to about 50 vol. % of the culture medium is replaced by fresh culture medium containing at least one neurotransmitter and/or from about 11 to about 100 ng/ml of at least one growth factor after from about 24 to about 48 h, particularly after 24 h, during the cultivation in method step b). Preferably used neurotransmitter and growth factors and preferred total quantities or concentrations are the transmitters, growth factors, total quantities or concentrations indicated above.

A second subject of the present disclosure relates to the use of at least one neurotransmitter and/or at least one growth factor for improvement of the culture conditions of cultures of primary sweat gland cells and/or three-dimensional sweat gland equivalents with from about 500 to about 500,000 sweat gland cells and a diameter of from about 100 to about 6000 µm. Use as contemplated herein leads to an increase of the expression of sweat-gland-specific marker proteins in these cultures. In this manner, a loss of function, which can occur due to the absence of or only low concentrations of these proteins, can be avoided during the cultivation.

Especially preferred embodiments of this object of the present disclosure are wherein at least one neurotransmitter or at least one growth factor, particularly exactly one neurotransmitter or exactly one growth factor is used.

With regard to the neurotransmitters and growth factors used as contemplated herein as well as with regard to the total quantity of neurotransmitters used, the statements apply mutatis mutandis for the method.

With regard to the total quantities of growth factors(s) it has been found to be advantageous if the at least one growth factor, particularly epidermal growth factor (EGF) is used in a total concentration of from about 1.0 ng/ml to about 30 ng/ml, preferably from about 3.0 ng/ml to about 20 ng/ml, more preferably from about 5.0 ng/ml to about 15 ng/ml, particularly from about 8.0 ng/ml to about 12 ng/ml.

With regard to other preferred embodiments of the disclosed use, the statements apply mutatis mutandis to the method.

The following examples explain the present disclosure without limiting it:

EXAMPLES

1 Preparation of the Culture of Primary Sweat Gland Cells and Three-Dimensional Sweat Gland Equivalents (Method Step a))

1.1 Isolation of Sweat Glands

The native seat glands were obtained from tissue samples, so-called biopsies, which were obtained from plastic surgery of patients who have approved the use of the material for research purposes. The tissue used was taken from upper arm and face lifting. The resulting eccrine and apocrine sweat glands from the underarm area were isolated.

For this purpose, each biopsy was divided into small parts and then cut into pieces with a maximum area of approximately 1 cm×1 cm. Then the digestion of the skin took place with a mixture of equal parts collegenase II (5 mg/ml) and thermolysin (0.25 mg/ml) at 37° C. in an incubator for approximately from about 3.5 to about 5 hours until the connective tissue was almost completely digested. This mixture was subsequently centrifuged at about 1200 rpm for 5 minutes and the excess material is discarded in order to remove the enzyme solution and the excess fat. The resulting pellet was placed in a DMEM solution and the solution transferred to a petri dish. Based on a microcapillary, intact sweat glands were isolated under a binocular loupe and transferred to a fresh DMEM medium.

1.2 Cultivation of the Isolated Native Sweat Glands and Production of the Culture of Primary Sweat Gland Cells The sweat glands isolated in step 1.1 were placed in collagen-I-coated culture bottles and then 25 ml of nutrient medium was added. After cultivation for from about 7 to about 21 days in an incubator at about 37° C. and about 5% $CO_2$, the growing sweat gland cells were detached and placed on collagen-I-coated culture bottles again until cultivated until confluence (monolayer culture of primary sweat gland cells).

The composition of the nutrient medium used is as follows:

| Components of the medium | |
| --- | --- |
| DMEM/Ham's F12 nutrient mix | 3:1 |
| Fetal calf serum (FCS) | 10% |
| EGF | 10 ng/ml |
| Hydrocortisone | 0.4 µg/ml |
| Insulin | 0.12 UI/ml |
| Choleratoxin | $10^{-10}$ M |
| Adenine | 2.43 g/ml |
| Gentamicin | 25 µg/ml |
| Penicillin G | 100 UI/ml |
| Triiodothyronine | $2 * 10^{-9}$ M |
| Ascorbyl-2-phosphate | 1 mM |

1.3 Production of Three-Dimensional Sweat Gland Equivalents

After determination of the exact cell counts of the aforementioned monolayer cultures of primary sweat gland cells, they were adjusted to a cell count of from about 10 to about 5,000 cells per µl using the aforementioned nutrient medium and then 50 µl portions of this cell suspension were each transferred to wells of a GravityPLUS® harvesting plate by employing the SureDrop® Inlet introduction system (both products of Inshpero AG, Switzerland). The cultivation takes place at from about 36 to about 38° C. and a $CO_2$ content of about 5 wt. % relative to the total weight of the atmosphere used for cultivation. After from about 1 to about 3 days, about 40 vol. % of the medium is replaced with fresh nutrient medium in each of the wells of the "GravityPLUS®" harvesting plate. After from about 2 to about 7 days of cultivation, the 3D sweat gland equivalents are harvested with an addition of from about 50 to about 200 of nutrient medium and transferred to a "GravityTRAP®" plate (Inshpero AG, Switzerland). Before the harvest, the "GravityTRAP®" plate is moistened with from about 60 to about 100 of keratinocytic medium by employing a multi-channel pipette in order to minimize the formation of air bubbles and avoid the loss of the three-dimensional sweat gland equivalents. After the harvest, the plate is centrifuged for from about 1 to about 5 minutes at from about 100 to about 300×g to remove air bubbles. Part of the three-dimensional sweat gland equivalent was analyzed, whereas another part was cultivated for an additional from about 1 to about 6 days in the recesses of the harvest plate at about 37° C. and about 5 wt. % $CO_2$ relative to the total weight of the atmosphere used for the cultivation.

2. Cultivation of the Primary Sweat Gland Cells and/or the Three-Dimensional Sweat Gland Equivalents (Method Step b))

The cell cultures of primary sweat gland cells and/or three-dimensional sweat gland equivalents produced in steps 1.2 and 1.3 above were each cultivated after addition of culture media K1 and K2 for about 48 h at about 37° C. and about 5 wt. % $CO_2$ relative to the total weight of the atmosphere used for cultivation. After about 24 h, about 40 vol. % of the respective culture medium K1 or K2 is replaced with fresh culture medium K1 or K2 and the cultivation is continued.

Culture medium K1: corresponding to the culture medium used under point 1.2, however, containing an additional from about 2.0 to about 50 µM of acetylcholine as a muscarinic neurotransmitter Culture medium K2: corresponding to the culture medium used under point 1.2, however, containing an additional from about 0.3 to about 20 mM of adenosine triphosphate (ATP) as a purinergic neurotransmitter

3 Identification and Analysis of the Gene Expression of Sweat-Gland-Specific Marker Proteins Detection of the sweat-gland-specific marker proteins indicated below can be determined, for example, using molecular-biological methods. In this context, the mRNA is first isolated using the "RNeasy Micro Kit" (Qiagen) according to the manufacturer's specifications and then analyzed by employing quantitative real-time PCR (Bellas et. al.: "In Vitro 3D Full-Thickness Skin-Equivalent Tissue Model Using Silk and Collagen Biomaterials"; Macromolecular Bioscience, 2012, 12, pages 1627-1636). However, it is also possible to analyze the marker proteins indicated below using protein-biochemical methods, such as Western Blot Analysis or ELISA (enzyme-linked immonosorbent assay).

In the cultures produced under point 2, significantly higher quantities of the sweat-gland-specific marker proteins Aquaporin 5 (AQPS), cystic fibrosis transmembrane conductance regulator (CFTR), $Ca_2$+-activated chloride channel (ANO1), sodium-potassium-chloride cotransporter 1 (NKCC2), carcinoembryonic antigen-related cell adhesion molecule 5 (CEACAM5), muscarinic acetylcholine receptor M3 ($Chrm_3$), are detected in comparison to cultures only using the culture medium described under point 1.2

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method of producing cultures of primary sweat gland cells and/or three-dimensional sweat gland equivalents, the method comprising:
   a) preparing a culture of primary sweat gland cells and/or a three-dimensional sweat gland equivalent in a culture medium, wherein the culture of primary sweat gland cells and/or equivalent comprises from about 500 to about 500,000 sweat gland cells and a diameter of from about 100 to about 6000 micrometers (µm);
   b) cultivating the culture of primary sweat gland cells and/or the three-dimensional sweat gland equivalent in the culture medium, wherein during cultivation the culture medium comprises a neurotransmitter.

2. The method according to claim 1, wherein the culture prepared in method step a) is the three-dimensional sweat gland equivalent culture.

3. The method according to claim 2, wherein the three-dimensional sweat gland equivalent prepared in method step a) comprises 1% or less by weight of a matrix compound other than matrix compounds produced by the three-dimensional sweat gland equivalent, based on a total weight of the three-dimensional sweat gland equivalent.

4. The method according to claim 2, wherein the three-dimensional sweat gland equivalent prepared in method step a) comprises a cell type selected from the group of coil cells, clear cells, dark cells, myoepithelium cells, duct cells and mixtures thereof.

5. The method according to claim 1, wherein the neurotransmitter is selected from the group of αβ-adrenergic transmitters, purinergic transmitters and mixtures thereof.

6. The method according to claim 1, wherein the culture medium used in method step b) comprises the neurotransmitter adenosine triphosphate (ATP) as a purinergic neurotransmitter.

7. The method according to claim 6, wherein the neurotransmitter comprises exactly one neurotransmitter.

8. The method according to claim 1, wherein the neurotransmitter is a compound that bonds on an ionotropic receptor.

9. The method according to claim 1, wherein the culture medium used in method step b) comprises the neurotransmitter acetylcholine as a muscarinic neurotransmitter.

10. A method of growing a culture of a three-dimensional sweat gland equivalent, the method comprising the steps of:
    a) preparing the three-dimensional sweat gland equivalent in a culture medium, wherein the three-dimensional sweat gland equivalent comprises 1% or less by weight of a matrix compound other than matrix compounds produced by the three-dimensional sweat gland equivalent, based on a total weight of the three-dimensional sweat gland equivalent; and
    b) cultivating the three-dimensional sweat gland equivalent in the culture medium, wherein during cultivation the culture medium comprises a neurotransmitter and/or a growth factor.

11. The method of claim 1, wherein:
cultivating the cell culture of primary sweat gland cells and/or the three-dimensional sweat gland equivalent in the culture medium comprises cultivating the cell culture wherein the culture medium comprises exactly one neurotransmitter during the cultivation.

12. The method of claim 9 wherein:
the neurotransmitter comprises exactly one neurotransmitter.

13. The method of claim 1 wherein:
cultivating the cell culture under step b) comprises cultivating the cell culture wherein the culture medium further comprises a growth factor during the cultivation.

14. The method of claim 1 wherein:
cultivating the cell culture of primary sweat gland cells and/or the three-dimensional sweat gland equivalent in the culture medium comprises cultivating the cell culture and/or the three-dimensional sweat gland equivalent wherein the culture medium during cultivation comprises the neurotransmitter in a total concentration of from about 2.0 micromolar (µM) to about 25 millimolar (mM).

15. The method of claim 13 wherein:
the culture medium comprises the growth factor in a total concentration of from about 11 nanograms per milliliter (ng/ml) to about 40 ng/ml during the cultivation.

16. The method of claim 13 wherein;
the culture medium comprises the growth factor in a total concentration of from about 15 nanograms per milliliter (ng/ml) to about 25 ng/ml during the cultivation.

17. The method of claim 10 wherein:
cultivating the three-dimensional sweat gland equivalent comprises cultivating the three-dimensional sweat gland equivalent wherein, during cultivation, the culture medium comprises a neurotransmitter.

18. The method of claim 17 wherein:
the neurotransmitter comprises adenosine triphosphate (ATP) as a purinergic neurotransmitter, and wherein the neurotransmitter comprises exactly one neurotransmitter.

19. The method of claim 17, wherein:
the neurotransmitter is selected from the group of αβ-adrenergic transmitters, purinergic transmitters and mixtures thereof.

20. The method of claim 10 wherein:
the three-dimensional sweat gland equivalent is a cell model of glandular cells which has an extent in all three spatial directions.

* * * * *